United States Patent [19]

Sasaki et al.

[11] Patent Number: 4,504,599

[45] Date of Patent: Mar. 12, 1985

[54] METHOD FOR PRODUCTION OR ACTIVATION OF ANTIMONY-CONTAINING METAL OXIDE CATALYSTS

[75] Inventors: Yutaka Sasaki; Yoshimi Nakamura, both of Kanagawa, Japan

[73] Assignee: Nitto Chemical Industry Co., Ltd., Tokyo, Japan

[21] Appl. No.: 551,741

[22] Filed: Nov. 14, 1983

[30] Foreign Application Priority Data

Nov. 12, 1982 [JP] Japan .................................. 57-197611

[51] Int. Cl.$^3$ ...................... B01J 23/10; B01J 23/18; B01J 23/72; B01J 23/84
[52] U.S. Cl. ..................................... 502/304; 502/202; 502/208; 502/215; 502/216; 502/219; 502/220; 502/222; 502/223; 502/241; 502/242; 502/243; 502/244; 502/247; 502/249; 502/311; 502/324; 502/325; 502/337; 502/338; 502/345; 502/350; 502/352; 502/353

[58] Field of Search ............... 502/202, 249, 304, 311, 502/352, 208, 215, 216, 219, 220, 222, 223, 241, 242, 243, 244, 247, 324, 325, 337, 338, 345, 350, 353

[56] References Cited

U.S. PATENT DOCUMENTS 4,290,920 9/1981 Suresh et al. .................... 502/304 X Primary Examiner—W. J. Shine
Attorney, Agent, or Firm—Sughrue, Mion, Zinn, Macpeak and Seas

[57] ABSTRACT

Antimony-containing metal oxide catalysts are produced or activated by dry blending (a) a catalyst or catalyst precursor composed of an antimony-containing metal oxides composition containing antimony and at least one element selected from the group consisting of iron, cobalt, nickel, manganese, cerium, uranium, tin, titanium, and copper, and (b) elemental antimony or an antimony compound, and contacting the components (a) and (b) with each other at about 300° C. to about 1000° C. in a non-reducing gas atmosphere for a period sufficient for the elemental antimony or antimony compound (b) to deposit on the catalyst or catalyst precursor (a).

14 Claims, No Drawings

METHOD FOR PRODUCTION OR ACTIVATION OF ANTIMONY-CONTAINING METAL OXIDE CATALYSTS

FIELD OF THE INVENTION

The present invention relates to a method for production or activation of antimony-containing metal oxide catalysts.

BACKGROUND OF THE INVENTION

It is well known that antimony-containing metal oxide catalysts containing antimony oxide and the oxide of at least one metal selected from the group consisting of iron, cobalt, nickel, manganese, cerium, uranium, tin, titanium, and copper are useful for oxidation, ammoxidation, or oxidative dehydrogenation of organic compounds. They are also useful for the production of aldehydes and acids through the oxidation of olefins and alcohols, for the production of nitriles through the ammoxidation of olefins and alcohols, and for the production of unsaturated compounds through the oxidative dehydrogenation of olefins and alcohols.

An oxide catalyst composed of antimony and at least one element selected from the group consisting of iron, cobalt and nickel is disclosed in Japanese Patent Publication No. 19111/1964. A catlyst composed of antimony oxide and tin oxide is disclosed in U.S. Pat. No. 3,152,170. A catalyst composed of antimony oxide and uranium oxide is disclosed in U.S. Pat. No. 3,308,151. Moreover, improvements in these catalysts have been proposed.

These conventional catalysts have good performance but are not necessarily satisfactory in the yield of the intended product.

It is known that the formation of an antimony-rich surface layer on the antimony-containing metal oxide catalyst is effective in improving the selectivity of the intended product. It is also known that the antimony-rich surface layer can be formed by impregnating an antimony-containing metal oxide catalyst with an antimony component. It is reported in Aso, et al., "*Shokubai*" (*Catalyst*) 21 (4) 304–306 (1979), that an antimony-rich surface layer is formed on an Fe-Sb catalyst upon calcination and that this improves the selectivity of acrolein through the oxidation of propylene. It is also reported that the selectivity of acrolein is improved by impregnating an FeSbO$_4$ catalyst with a small amount of antimony component.

According to Y. Boudeville et al., *Journal of Catalysis* 58 (1) 52–60 (1979), Y. M. Cross et al., *Journal of Catalysis* 58 (1) 61–67 (1979), and H. J. Herniman, et al., *Journal of Catalysis* 58 (1) 68–73 (1979), an antimony-rich layer is formed on the surface of an Sn-Sb catalyst depending on the high temperature treatment of calcination in the course of preparation. The layer thus formed improves the selectivity of acrolein in the oxidation of propylene and the selectivity of butadiene in the oxidative dehydrogenation of butene. There is proposed in U.S. Pat. No. 4,290,920 a method for increasing the yield of the intended product by impregnating an antimony-containing oxide complex catalyst with an Sb component.

Since it is known that the formation of an antimony-rich surface layer is effective in improving the selectivity of the intended product, it has been proposed to improve the selectivity of the intended product by the impregnation of an antimony component. However, previous methods of impregnating a catalyst with an antimony component have the disadvantage that they are not easily applied to the industrial production of catalysts.

According to the above-mentioned report by Aso et al., a suspension of antimonic acid is used for the impregnation of an antimony component. It is difficult to perform uniform impregnation with a suspension except in the case where the catalyst to be impregnated has a large pore diameter. The method disclosed in U.S. Pat. No. 4,290,920 does not insure uniform impregnation.

In the production of a fluidized-bed catalyst by the impregnation of an antimony component, the desired amount of antimony is dissolved in a limited quantity of liquid corresponding to the pore volume of the catalyst, and the catalyst undergoes impregnation, drying, and calcination. In actuality, however, it is difficult to prepare a solution containing as much antimony as required, because only a small number of water-soluble antimony compounds which can be dissolved in a limited quantity of water exit. A solution of highly soluble Sb halide dissolved in hydrochloric acid causes corrosion of equipment and cannot be used industrially. On the other hand, an aqueous solution of a complex of antimony trioxide with tartaric acid or ethylene glycol is also industrially impractical, because the organic component reduces the catalyst in the subsequent calcination process and gives off an undesirable decomposition gas.

Uniform impregnation cannot be achieved with a suspension instead of a solution, because the antimony component (suspensoid) deposits on the surface of the catalyst particles and the suspending medium penetrates into the pores of the catalyst. Thus, the resulting catalyst is poor in performance and reproducibility. In addition, these impregnation methods have the common disadvantage that the production process is long and the productivity is extremely low. Such a production process typically requires the preparation of a catalyst precursor and the impregnation, drying, and calcination of the precursor.

SUMMARY OF THE INVENTION

The invention overcomes the above-described problems encountered in producing antimony-containing metal oxide catalysts, by providing a novel method for producing or activating such catalysts without the previously required steps of aqueous impregnation, drying, and calcination of a precursor.

It is an object of this invention to provide a method for the production or activation of antimony-containing metal oxide catalysts without resort to the above-mentioned impregnation method. Another object of the invention is to produce or to activate a catalyst that exhibits improved selectivity of the intended product.

These objects are achieved according to the method of this invention, by producing or activating an antimony-containing metal oxide catalyst by the steps of dry blending (a) catalyst precursor or a catalyst composed of antimony-containing metal oxides and (b) elemental antimony or an antimony compound, and heating the resulting mixture in a non-reducing gas atmosphere at about 300° to 1000° C. for a period of time sufficient for the antimony component to deposit on the catalyst.

DETAILED DESCRIPTION OF THE INVENTION

An advantage of the present invention is that the method of this invention does not require an impregnating solution or special equipment or a new process. According to the method of this invention, catalysts of high performance can be made with good reproducibility.

Another advantage is that the method of this invention can be applied to a fresh (unused) antimony-containing metal oxide catalyst or a precursor thereof ("production" of catalysts), and also to a used catalyst ("activation" or "regeneration" of catalysts).

A further advantage of the present invention is that the process used in this invention is simple; that is, an antimony-containing metal oxide catalyst is mixed with elemental antimony or an antimony compound and the resulting mixture is heated in an non-reducing gas atmosphere. Because of its simplicity this invention is industrially valuable.

Composition of Antimony-containing Metal Oxide Catalyst

The catalyst to be produced or activated in this invention includes any of the known antimony-containing metal oxide catalysts described in the above-mentioned patents, containing antimony oxide and the oxide of at least one metal selected from the group consisting of iron, cobalt, nickel, manganese, cerium, uranium, tin, titanium and copper.

The preferred antimony-containing metal oxide catalysts used in this invention have a composition represented by the following empirical formula:

$$Me_aSb_bX_cQ_dR_eO_f(SiO_2)_g$$

where,

Me is at least one element selected from the group consisting of Fe, Co, Ni, Mn, Ce, U, Sn, Ti, and Cu;

X is at least one element selected from the group consisting of V, Mo, and W;

Q is at least one element selected from the group consisting of Li, Na, K, Rb, Cs, Be, Mg, Ca, Sr, Ba, Y, La, Th, Zr, Hf, Nb, Ta, Cr, Re, Ru, Os, Rh, Ir, Pd, Pt, Ag, Zn, Cd, Al, Ga, In, Tl, Ge, Pb, As, S, and Se;

R is at least one element selected from the group consisting of B, P, Te, and Bi;

the subscripts a, b, c, d, e, f, and g denote the atomic ratio in the following range:

$a = 5$ to 15,
$b = 5$ to 100,
$c = 0$ to 15,
$d = 0$ to 50,
$e = 0$ to 10,
$f = $ a number corresponding to the oxides formed by the combination of the above components, and
$g = 0$ to 200.

These catalysts may be used as such or may be supported on a carrier such as silica, alumina, silica-alumina, silica-titania, titania, or zirconia.

These oxide compositions can be prepared by using known methods disclosed in U.S. Pat. Nos. 3,341,471, 3,657,155, 3,686,138 and 4,107,085.

According to the method of this invention, the dry blending and heating are preferably performed under fluidized conditions; therefore, the antimony-containing metal oxide catalyst is preferably calcined at about 400° C. to about 1,000° C. for 1 to 50 hours, in order to give the catalyst sufficient mechanical strength.

The method of this invention can be applied to antimony-containing metal oxide catalysts which have been used in reactions or which have been degraded after use in reactions.

The method of this invention is preferably performed in fluidized conditions so that the contacting of the catalyst or catalyst precursor with the antimony or antimony compound is performed well and the antimony component deposits evenly on the catalyst.

For use in fluidized-bed reactors, the antimony-containing metal oxide composition (as the catalyst or catalyst precursor) preferably has a particle diameter of about 5 to 300 microns and a weight mean median diameter of about 20 to 200 microns.

Antimony or Antimony Compound

The elemental antimony used for the method of this invention is prepared by crushing or molding metallic antimony to a proper size. In the case where this invention is practiced by using a solid antimony component in the fluidized condition, it should have a particle diameter of about 0.1 to about 500 microns and a weight mean median diameter of about 0.5 to about 500 microns. If the particle diameter is too small, the solid antimony component escapes; and if it is too large, the solid antimony component does not mix well with the catalyst or catalyst precursor and the deposit of antimony component is incomplete. The antimony compound used in the method of this invention includes a volatile substance with a vapor pressure sufficiently high to deposit on the catalyst or catalyst precursor under treating condition or a compound capable of conversion into the volatile substance, for example, antimony oxides such as antimony trioxide, antimony tetroxide, and antimony pentoxide; antimony oxide hydrates and salts thereof such as antimonous acid and antimonic acid; antimony sulfide, antimony selenide, antimony telluride, antimony sulfate, antimony halide, antimony oxyhalide, antimonide, antimony salts of carboxylic acid and sulfonic acid, and stibine and other organic antimony compounds.

An antimony compound having a high vapor pressure can be fed together with a fluidizing gas. An antimony compound which is solid at ordinary temperature or higher can be mixed in the form of powder.

The antimony component may be supported on a carrier or the catalyst.

Production or Activation of Catalyst

According to the method of this invention, the production or activation of the antimony-containing metal oxide catalyst is accomplished by contacting an antimony-containing metal oxide catalyst and elemental antimony or an antimony compound with each other at a high temperature in a non-reducing atmosphere.

The method of this invention can be applied not only to catalysts for fluidized-bed reactors but also to catalysts for fixed-bed reactors and moving-bed reactors. Best results are obtained when an antimony-containing metal oxide composition used to produce a fluidized-bed catalyst is treated according to the method of this invention.

The calcination should preferably be carried out by using a rotary calcining oven or fluidized calcining oven. The latter is preferred because the contact of antimony-containing metal oxide composition and antimony component is accomplished uniformly. For uniform mixing, the antimony-containing metal oxide composition should have a particle diameter of about 5 to about 300 microns and a weight mean median diameter of about 20 to about 200 microns, and the solid antimony component should have a particle diameter of about 0.1 to about 500 microns and a weight mean median diameter of about 0.5 to about 500 microns.

The effect of this invention is produced as the result of the deposition of the antimony component on the catalyst. If the quantity of antimony is too small, no effect is produced, and if antimony is used in an excessive amount, the reaction rate will decrease and the catalyst will be adversely affected. The quantity of antimony to be added, or the apparent increase of antimony content should be 0.01 to 20 wt.%, and preferably 0.05 to 10 wt.%.

The apparent increase of antimony content is defined as follows:

$$\text{Apparent increase of antimony (\%)} = \frac{\text{weight of antimony added (g)}}{\text{weight of antimony-containing metal oxides composition (g)}} \times 100$$

The preferred quantity of the antimony component to be added varies depending on the properties of the antimony component. In the case where the antimony component is used in the vapor phase, or where the antimony component is volatile or capable of conversion into a volatile substance under the treating conditions, the calculated quantity of antimony should be added. In the case of an antimony component which is slow to transfer to the catalyst, the quantity of antimony should be slightly increased over the amount calculated.

In the case where the antimony component is used in solid form, it may be dry-blended with the catalyst or a precursor thereof prior to treatment, or may be added and mixed during treatment.

The treatment should be carried out under a non-reducing gaseous atmosphere. "Non-reducing" means that the atmoshpere does not reduce and degrade the catalyst or a precursor thereof under treating conditions.

The non-reducing gas used is not unduly limited and may be freely selected from those known in the art. Typical examples of non-reducing gases include air, oxygen, nitrogen, helium, argon, carbon dioxide, carbon monoxide, steam, and nitrogen oxide, and a mixture of oxygen and at least one reducing material selected from hydrogen, ammonia, methanol, hydrocarbons, and other organic compounds.

Where a reducing gas is used alone, the catalyst or catalyst precursor is irreversibly reduced and antimony is removed from the catalyst matrix. As a result, the catalyst is degraded.

The temperature and time for treatment can be varied according to the source of antimony to be used. If the antimony source is volatile, the temperature may be low and the time may be short; but if it is less volatile, the temperature is somewhat higher and the time is somewhat longer. Typically treatment is performed at a temperature of about 300° C. to about 1000° C. for about 0.5 to about 50 hours. If the temperature is lower than about 300° C., the effect is diminished and if it is higher than 1000° C., the catalyst exhibits decreased activity.

The selectivity of the intended product is improved by depositing an antimony component on the surface of the catalyst as mentioned above. In a preferred embodiment the effect is further increased and the activity lasts longer when the catalyst is calcined at about 400° C. to about 950° C. under a non-reducing atmosphere.

It is theorized that the deposited antimony component reacts with the catalyst or catalyst precursor to form stable active sites thereon.

In this specification, the yield and selectivity of the intended product are defined as follows:

$$\text{Yield (\%)} = \frac{\text{Weight of carbon in intended product formed (g)}}{\text{Weight of carbon in feed stock organic compound fed (g)}} \times 100$$

$$\text{Selectivity (\%)} = \frac{\text{Weight of carbon in intended product formed (g)}}{\text{Weight of carbon in feed stock organic compound reacted (g)}} \times 100$$

Unless otherwise indicated herein, all parts, percentages, ratios and the like are by weight.

The present invention is illustrated in greater detail by reference to the following examples. However, this invention is not to be construed as being limited to these examples. Catalytic activity was tested under the following conditions.

(1) Ammoxidation of propylene

The catalyst is filled in a fluidized-bed reactor having a bed diameter of 2.5 cm and a bed depth of 40 cm, and a gas of the following composition is fed. The reaction is carried out at atmospheric pressure.

$O_2$ (air)/propylene = 2.2 (mol/mol)

$NH_3$/propylene = 1.1 (mol/mol)

(2) Ammoxidation of isobutene

The same reactor as used for ammoxidation of propylene is used, and a gas of the following composition is fed. The reaction is carried out at atmospheric pressure.

$O_2$ (air)/isobutene = 3.0 (mol/mol)

$NH_3$/propylene = 1.3 (mol/mol)

EXAMPLE 1

A fluidized-bed catalyst having an empirical formula of $Fe_{10}Sb_{25}W_{0.25}O_{65.8}(SiO_2)_{30}$ was tested for activity under the above-mentioned condition (1). The yield of acrylonitrile was 71%.

With this catalyst was mixed antimony trioxide power in such an amount that the apparent increase of antimony content was 1.0%, and the resulting mixture was kept at 500° C. for 3 hours while fluidizing with air containing 10% ammonia.

The thus treated catalyst was tested for activity under the above-mentioned condition (1), and the yield of acrylonitrile was 75%.

EXAMPLE 2

A fluidized-bed catalyst having an empirical formula of $Sn_{10}Sb_{60}O_{140}(SiO_2)_{30}$ was tested for activity under the above-mentioned condition (1). The yield of acrylonitrile was 63%.

With this catalyst was mixed an antimony-containing powder (prepared as mentioned below) in such an amount that the apparent increase of antimony content was 0.8%, and the resulting mixture was kept at 500° C. for 2 hours while fluidizing with nitrogen.

The thus treated catalyst was treated for activity under the above-mentioned condition (1), and the yield of acrylonitrile was 70%.

The antimony-containing powder was prepared by dissolving antimony trioxide in an aqueous solution of ammonium tartrate, adding silica sol, spray drying, and calcining at a temperature of 300° C. for 2 hours. The weight ratio of $Sb_2O_3/SiO_2$ was 0.05.

EXAMPLE 3

A fluidized-bed catalyst having an empirical formula of $U_{10}Sb_{50}W_{0.1}Te_{0.5}O_{67.8}(SiO_2)_{60}$ was treated for activity under the above-mentioned condition (1). The yield of acrylonitrile was 73%.

With this catalyst was mixed metallic antimony powder in such an amount that the apparent increase of antimony content was 1.5%, and the resulting mixture was kept at 450° C. for 2 hours while fluidizing with air. The thus treated catalyst was tested for activity under the above-mentioned condition (1), and the yield of acrylonitrile was 79%.

EXAMPLE 4

A composition calcined at 500° C. having an empirical formula of $Fe_{10}Sb_{25}W_{0.25}Te_{1.0}O_{67.8}(SiO_2)_{30}$ was calcined while fluidizing with air under the following three conditions.

(1) at 820° C. for 5 hours.
(2) at 830° C. for 5 hours.
(3) at 840° C. for 5 hours.

The resulting catalysts were tested for activity under the above-mentioned condition (1), and the yields were 79%, 80%, and 78%, respectively.

With the same composition calcined at 500° C. described above was mixed antimony trisulfide powder in such an amount that the apparent increase of antimony content in each of the catalysts was 0.7%. The resulting mixtures were calcined at 790° C. for 5 hours while fluidizing with air. The thus treated catalysts were tested for activity under the above-mentioned condition (1), and the yield of acrylonitrile was 82%.

EXAMPLE 5

The same composition as used in Example 4 was initially calcined while fluidizing with air at 790° C. for 5 hours.

The resulting catalyst was tested for activity under the above-mentioned condition (1), and the yield of acrylonitrile was 75%.

With the catalyst was mixed antimony pentoxide powder in such an amount that the apparent increase of antimony content was 1.5%. The resulting mixture was kept at 450° C. for 3 hours while fluidizing with air containing 5% methanol. The thus treated catalyst was tested for activity under the above-mentioned condition (1), and the yield of acrylonitrile was 81%.

EXAMPLE 6

A deactivated catalyst having an empirical formula of $W_{0.5}Te_{1.0}Fe_{10}Sb_{25}O_{68.5}(SiO_2)_{30}$ was tested for activity under the above-mentioned condition (1), after it had been used in ammoxidation reaction of propylene for a long time to become deactivated. The yield of acrylonitrile was 76%.

With this catalyst was mixed antimony trioxide in such an amount that the apparent increase of antimony content was 0.4%. The thus treated catalyst was tested for activity under the above-mentioned condition (1), and the yield of acrylonitrile increased to 78.5%.

EXAMPLE 7

A fluidized-bed catalyst having an empirical formula of $Fe_{10}Sb_{23}Cu_{3.5}W_{0.2}Mo_{0.4}Te_{1.3}O_{68.9}(SiO_2)_{60}$ was tested for activity under the above-mentioned condition (1). The yield of acrylonitrile was 80%.

With this catalyst was mixed antimony trioxide powder in such an amount that the apparent increase of antimony content was 1.5%, and the resulting mixture was kept at 500° C. for 2 hours while fluidizing with helium.

The thus treated catalyst was tested for activity under the above-mentioned condition (1), and the yield of acrylonitrile increased to 81%. The treated catalyst was further calcined at 750° C. for 4 hours while fluidizing with air. The yield of acrylonitrile increased to 82.5%.

EXAMPLE 8

A fluidized bed catalyst having an empirical formula of $Mo_1Te_2Cu_4Fe_{10}Sb_{23}O_{72}(SiO_2)_{60}$ was tested for activity under the above-mentioned condition (2). The yield of methacrylonitrile was 70%.

With this catalyst was mixed metallic antimony powder in such an amount that the apparent increase of antimony content was 1.0%, and the resulting mixture was kept at 480° C. for 3 hours while fluidizing with air.

Using the thus treated catalyst, the ammoxidation of isobutene was carried out under the above-mentioned condition (2), and the yield of methacrylonitrile increased to 72%.

TABLE

| | Catalyst composition (atomic ratio) | Antimony component added | | Results of activity tests | | | |
|---|---|---|---|---|---|---|---|
| | | Apparent increase of Sb (%) | Component/ gas atmosphere | Reaction temperature (°C.) | Contact time (sec) | Yield of acrylonitrile (%) | Conversion of propylene (%) |
| Example 1 | $Fe_{10}Sb_{25}W_{0.25}O_{65.8}-(SiO_2)_{30}$ | | | | | | |
| | A. Not treated | | | 460 | 5 | 71 | 99 |
| | B. Treated | 1.0 | Antimony trioxide/ammonia-air | 470 | 5 | 75 | 97 |
| Example 2 | $Sn_{10}Sb_{60}O_{140}(SiO_2)_{30}$ | | | | | | |
| | A. Not treated | | | 460 | 6 | 63 | 94 |
| | B. Treated | 0.8 | Sb-containing powder/ nitrogen | 470 | 6 | 70 | 96 |
| Example 3 | $U_{10}Sb_{50}W_{0.1}Te_{0.5}-$ | | | | | | |

TABLE-continued

| | Catalyst composition (atomic ratio) | Antimony component added | | Results of activity tests | | | |
|---|---|---|---|---|---|---|---|
| | | Apparent increase of Sb (%) | Component/ gas atmosphere | Reaction temperature (°C.) | Contact time (sec) | Yield of methacrylonitrile (%) | Conversion of isobutene (%) |
| | $O_{67.8}(SiO_2)_{60}$ | | | | | | |
| | A. Not treated | | | 470 | 5 | 73 | 95 |
| | B. Treated | 1.5 | Metallic antimony/air | 480 | 5 | 79 | 97 |
| Example 4 | $Fe_{10}Sb_{25}W_{0.25}Te_{1.0}-$ $O_{67.8}(SiO_2)_{30}$ | | | | | | |
| | A. Not treated Calcined | | | | | | |
| | at 820° C. for 5 hr | | | 460 | 5 | 79 | 98 |
| | at 830° C. for 5 hr | | | 470 | 5 | 80 | 98 |
| | at 840° C. for 5 hr | | | 470 | 6 | 78 | 96 |
| | B. Treated | 0.7 | Antimony trisulfide/air | 460 | 5 | 82 | 98 |
| Example 5 | $Fe_{10}Sb_{25}W_{0.25}Te_{1.0}-$ $O_{67.8}(SiO_2)_{30}$ | | | | | | |
| | A. Not treated | | | 450 | 4 | 75 | 96 |
| | B. Treated | 1.5 | Antimony pentoxide/methanol-air | 460 | 4 | 81 | 98 |
| Example 6 | $W_{0.5}Te_{1.0}Fe_{10}Sb_{25}-$ $O_{68.5}(SiO_2)_{30}$ | | | | | | |
| | A. Not treated | | | 460 | 6 | 76 | 97 |
| | B. Treated | 0.4 | Antimony trioxide/propylene-ammonia-air | 465 | 6 | 78.5 | 98 |
| Example 7 | $Fe_{10}Sb_{23}Cu_{3.5}W_{0.2}Mo_{0.4}-$ $Te_{1.3}O_{68.9}(SiO_2)_{60}$ | | | | | | |
| | A. Not treated | | | 435 | 5 | 80 | 99 |
| | B. Treated (1) | 1.5 | Antimony trioxide/helium /air | 435 | 5 | 81 | 97 |
| | Treated (2) | | | 440 | 5 | 82.5 | 99 |

| | Catalyst composition (atomic ratio) | Antimony component added | | Results of activity tests | | | |
|---|---|---|---|---|---|---|---|
| | | Apparent increase of Sb (%) | Component/ gas atmosphere | Reaction temperature (°C.) | Contact time (sec) | Yield of methacrylonitrile (%) | Conversion of isobutene (%) |
| Example 8 | $Mo_1Te_2Cu_4Fe_{10}Sb_{23}-$ $O_{72}(SiO_2)_{60}$ | | | | | | |
| | A. Not treated | | | 410 | 2.5 | 70 | 97 |
| | B. Treated | 1.0 | Metallic antimony/air | 420 | 2.5 | 72 | 97 |

While the invention has been described in detail and with reference to specific embodiments thereof, it will be apparent to one skilled in the art that various changes and modifications can be made therein without departing from the spirit and scope thereof.

What is claimed is:

1. A method for producing or activating antimony-containing metal oxide catalysts comprising the steps of dry blending (a) an antimony-containing metal oxide catalyst or catalyst precursor containing as essential ingredients (1) antimony and (2) at least one element selected from the group consisting of iron, cobalt, nickel, manganese, cerium, uranium, tin, titanium, and copper with (b) elemental antimony or a second antimony compound at about 300° C. to about 1000° C. in a non-reducing gas atmosphere for a period sufficient for antimony from said elemental antimony or second antimony compound (b) to deposit on said catalyst or catalyst precursor (a), wherein the apparent increase of antimony content in the antimony-containing metal oxide catalyst or catalyst precursor (a) as a result of depositing is 0.01 to 20 wt%.

2. The method according to claim 1, wherein the catalyst or catalyst precursor (a) is in the form of fluidized-bed particles and the catalyst or catalyst precursor (a) is dry blended with the elemental antimony or antimony compound (b) while the catalyst or catalyst precursor (a) is fluidized.

3. The method according to claim 1, wherein the antimony-containing metal oxide catalyst or catalyst precursor (a) before activation is represented by the following empirical formula:

$$Me_aSb_bX_cQ_dR_eO_f(SiO_2)_g$$

where,

Me is at least one element selected from the group consisting of Fe, Co, Ni, Mn, Ce, U, Sn, Ti, and Cu;

X is at least one element selected from the group consisting of V, Mo, and W;

Q is at least one element selected from the group consisting of Li, Na, K, Rb, Cs, Be, Mg, Ca, Sr, Ba, Y, La, Th, Zr, Hf, Nb, Ta, Cr, Re, Ru, Os, Rh, Ir, Pd, Pt, Ag, Zn, Cd, Al, Ga, In, Tl, Ge, Pb, As, S, and Se;

R is at least one element selected from the group consisting of B, P, Te, and Bi; and each subscript a, b, c, d, e, f, and g denotes the atomic ratio and has the following values a = 5 to 15,
b = 5 to 100,
c = 0 to 15,
d = 0 to 50,
e = 0 to 10,
f = a number corresponding to the oxides formed by combination of the above components, and
g = 0 to 200.

4. The method according to claim 1, wherein the elemental antimony is metallic antimony.

5. The method according to claim 1, wherein the second antimony compound is at least one member selected from the group consisting of, antimony trioxide, antimony tetroxide, antimony pentoxide, antimony oxide hydrates, antimony oxide hydrate salts, antimonous acid, antimonic acid, antimony sulfide, antimony selenide, antimony telluride, antimony sulfate, antimony halide, antimony oxyhalide, antimonoide, antimony salts of carboxylic acid, antimony salts of sulfonic acid, or stibine.

6. The method according to claim 5, wherein the second antimony compound is at least one member selected from the group consisting of antimony trioxide, antimony tetroxide, or antimony pentoxide.

7. The method according to claim 1, wherein the non-reducing gas atmosphere is a gas comprising at least one gas that is oxidizing or non-reducing for the antimony-containing metal oxide catalyst.

8. The method according to claim 7, wherein the non-reducing gas atmosphere comprises at least one gas selected from the group consisting of air, oxygen, nitrogen, helium, argon, carbon dioxide, or carbon monoxide.

9. The method according to claim 7, wherein the non-reducing gas atmosphere comprises oxygen and at least one gas selected from the group consisting of hydrogen, and ammonia.

10. The method according to claim 1, wherein after the contacting of the catalyst or catalyst precursor (a) with said elemental antimony or second antimony compound (b), the resulting composition is further calcined at about 400° C. to about 950° C. in a non-reducing atmosphere.

11. The method according to claim 1, wherein the particle diameter of the catalyst or catalyst precursor (a) is about 5 to about 300 microns and the weight mean median diameter of the catalyst or catalyst precursor (a) is about 20 to about 200 microns.

12. The method according to claim 1, wherein the elemental antimony or second antimony compound (b) is solid, has a particle diameter of about 0.1 to about 500 microns, and has a weight mean median diameter of about 0.5 to about 500 microns.

13. The method according to claim 1, wherein the second antimony compound is an organic antimony compound.

14. The method according to claim 7, wherein the non-reducing gas atmosphere is a gaseous organic compound.

* * * * *